(12) United States Patent
Feith

(10) Patent No.: US 8,048,345 B2
(45) Date of Patent: Nov. 1, 2011

(54) ZIRCONIUM OXIDE-BASED DENTAL IMPLANT AND METHOD FOR PRODUCING SAID DENTAL IMPLANT

(75) Inventor: Johan Feith, Euresburg/Achmühle (DE)

(73) Assignee: ZV3-Zircon Vision GmbH, Wolfratshausen (DE)

( * ) Notice: Subject to any disclaimer, the term of this patent is extended or adjusted under 35 U.S.C. 154(b) by 17 days.

(21) Appl. No.: 11/570,257

(22) PCT Filed: Jun. 3, 2005

(86) PCT No.: PCT/EP2005/006010
§ 371 (c)(1),
(2), (4) Date: Apr. 12, 2007

(87) PCT Pub. No.: WO2005/120386
PCT Pub. Date: Dec. 22, 2005

(65) Prior Publication Data
US 2008/0057475 A1  Mar. 6, 2008

(30) Foreign Application Priority Data
Jun. 8, 2004  (DE) .......... 10 2004 027 959

(51) Int. Cl.
*A61C 13/08* (2006.01)
*A61C 8/00* (2006.01)
*B28B 1/48* (2006.01)
*B28B 11/18* (2006.01)
*B28B 17/00* (2006.01)
*B29D 19/08* (2006.01)

(52) U.S. Cl. ........ 264/19; 264/154; 264/162; 433/201.1

(58) Field of Classification Search .......... 433/172–176, 433/201.1, 202.1–212.1; 428/542.8; 29/896.11; 264/16–20, 154, 162
See application file for complete search history.

(56) References Cited

U.S. PATENT DOCUMENTS 4,854,873 A * 8/1989 Linden .......... 433/173
6,217,333 B1  4/2001 Ercoli
(Continued)

FOREIGN PATENT DOCUMENTS

DE  19530981 A1  2/1997
(Continued)

OTHER PUBLICATIONS

Mechanical Properties of Dental Zirconia Ceramics Changed with Sandblasing and Heat Treatement; Dental Materials Journal 2008; 27(3):408-414.
(Continued)

*Primary Examiner* — Todd Manahan
*Assistant Examiner* — Matthew Nelson
(74) *Attorney, Agent, or Firm* — Panitch Schwarze Belisario & Nadel LLP

(57) ABSTRACT

A dental implant for a patient includes an anchoring part to anchor the dental implant in the bone and an abutment that is designed for fixation of a crown or similar supraconstruction and is or can be connected to the anchoring part. The anchoring part and the abutment are manufactured on a zirconium-oxide basis. The anchoring part and the abutment have special sections corresponding to the individual dimensions of the patient's bone and/or gums, said sections comprising a roughened surface designed to promote bone fusion. The special sections are produced on the green compact before the latter is finally sintered.

3 Claims, 2 Drawing Sheets

U.S. PATENT DOCUMENTS

| | | | |
|---|---|---|---|
| 7,011,522 B2 * | 3/2006 | Panzera et al. | 433/215 |
| 7,655,586 B1 * | 2/2010 | Brodkin et al. | 501/103 |
| 2002/0155412 A1 | 10/2002 | Panzera et al. | |
| 2003/0104337 A1 | 6/2003 | Cottrell | |
| 2003/0104338 A1 * | 6/2003 | Cottrell | 433/173 |
| 2005/0023710 A1 * | 2/2005 | Brodkin et al. | 264/16 |

FOREIGN PATENT DOCUMENTS

| | | | |
|---|---|---|---|
| DE | 10065971 A1 * | 6/2002 | |
| DE | 10159683 A1 | 6/2003 | |
| EP | 1529498 A1 | 5/2005 | |
| WO | WO 2004/020921 A1 * | 3/2004 | |
| WO | WO 2004021921 A1 * | 3/2004 | |

OTHER PUBLICATIONS

Abstract of SEM Evaluation of the Effect of Alumina-Sandblasting on Zirconia Surfaces; IADR General Session; Miami, Florida, Apr. 1-4, 2009.

State of the art of oral implants; Periodontology 2008; 47:15-26.

* cited by examiner

ZIRCONIUM OXIDE-BASED DENTAL IMPLANT AND METHOD FOR PRODUCING SAID DENTAL IMPLANT

CROSS-REFERENCE TO RELATED APPLICATIONS

This application is a Section 371 of International Application No. PCT/EP2005/006010, filed Jun. 3, 2005, which was published in the German language on Dec. 22, 2005, under International Publication No. WO2005/120386 A1, the disclosure of which is incorporated herein by reference.

BACKGROUND OF THE INVENTION

The invention relates to a dental implant.

For some time dental implants have been successfully employed. In many cases the material used for them is titanium, with which secure osteogenic fusion can be achieved. However, problems with their visual appearance can be avoided only by taking very elaborate measures.

From the document DE 101 59 683 a dental implant of the kind cited above is known in which the transition between the implant, the abutment and the supraconstruction seated thereon does not present any such aesthetic problems, because the material used there is based on zirconium oxide. What is problematic here is the fact that implants "ready-made" in this way must be stored in many different variants by the dental technician or at the factory, so that after the appropriate measurements of the patient have been made, the best-fitting implant can be selected. Even so, an optimal fitting is hardly possible.

BRIEF SUMMARY OF THE INVENTION

It is an objective of the present invention to provide a dental implant which is an improvement over those cited above, and to provide a method of manufacturing said implant, in order to ensure optimal fitting combined with easy insertion and characteristics promoting a long service life.

According to one aspect of the present invention there is provided a dental implant for a patient that comprises an anchoring part for anchoring the dental implant in the bone and an abutment for fixation of a crown or similar supraconstruction that is or can be connected to the anchoring part, in which the anchoring part and abutment are constructed on the basis of zirconium oxide, the anchoring part and/or the abutment comprising separate sections that correspond to individual dimensions of the patient's bone and/or gums and have a roughened surface designed to promote fusion with the bone and/or ingrowth into the gum tissue, the special sections being provided on the green compact prior to its final sintering.

The basis of the invention resides in the fact that only roughly ready-made green compacts (anchoring part and abutment) must be stored, while the surface processing necessary for osteogenic fusion can be performed in the dental laboratory, according to the measurements obtained there (tomographic images). Because this processing is done on the green compact, the surface can be roughened to an optimal degree, which would be nearly impossible for a finally sintered product on account of its great hardness. As a result of this individual surface configuration, even bone defects can be compensated by osteogenesis in an optimal way.

Preferably the special sections on the surface of the green compact are roughened by means of sand blasting. This technique is very simple and produces a surface roughness that optimally promotes osteogenesis.

The anchoring part and the abutment in one preferred embodiment of the invention are constructed as a single piece. This not only achieves optimal durability, but furthermore also results in an implant that is aesthetically optimal.

The transition region between the anchoring part and the abutment is preferably finished according to the individual dimensions of the patient's bone, in particular by processing the green compact. As a result, the individual conditions can be particularly well accommodated.

In one embodiment of the invention the anchoring part comprises a surface designed to be driven into a cylindrical or conical bore in the bone, as well as a concentric bore to receive a pin for the purpose of holding, guiding and driving in the anchoring part. This makes it possible to insert the implant especially precisely, with no need to employ elaborate templates or adjustment devices. In the case of an integral construction of anchoring part and abutment, the bore preferably runs through the abutment into the anchoring part, enabling the implant to be inserted exactly.

The anchoring part in one embodiment of the invention is preferably made separate from the abutment and comprises a coaxial bore, which on one hand again serves for driving in by means of a pin and on the other hand can be used for fixation of the abutment provided with a corresponding pin.

The bore is constructed, in particular comprising an expansion at its upper end, so that it can be closed off by a silicone stopper during a period of time during which the gum tissue is healing, after the anchoring part has been driven into the bone.

According to a second aspect of the present invention there is provided a method of producing a dental implant that comprises the following steps:

Production of a 3-dimensional digital image of a region of a patient's bone and gums into which the dental implant is to be inserted, Making a digital representation of the dental implant, Milling a zirconium-oxide green compact that corresponds to the dental implant but is overdimensioned to compensate shrinkage, Sand blasting of special sections of the green compact according to the digital image and digital representation, Where appropriate, producing bores in the green compact and Burning/sintering the processed green compact.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 3 is a sketch to assist with explanation of how the dental implant is driven in.

DETAILED DESCRIPTION OF THE INVENTION

Figure 1:
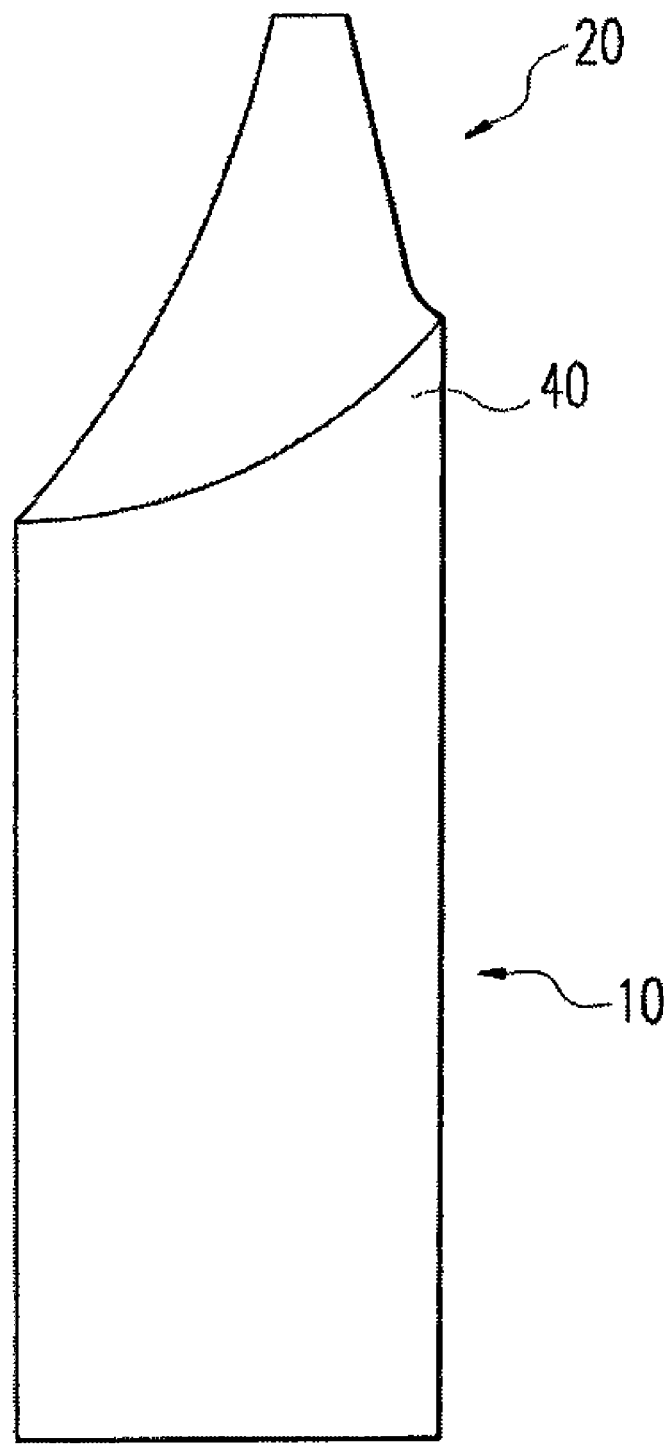
FIG. 1 is a side view of an embodiment of dental implant, according to the invention.

In the following description, the same reference numerals are used for identical parts and parts with identical actions.

As shown in FIG. 1, the dental implant consists of an anchoring part 10 to anchor the dental implant in the bone, as well as an abutment 20 onto which the supraconstruction is set in a manner already known. The anchoring part comprises special sections 40, in particular in the region of the transition between anchoring part 10 and abutment 20, which have been produced on the green compact by sand blasting, in accordance with the patient's data.

Figure 2:
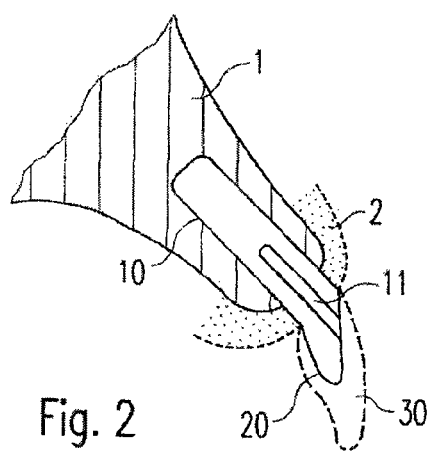
FIG. 2 is a schematic representation of the dental implant shown in FIG. 1 when inserted and in which bone and gum tissue are represented.
Figure 3:
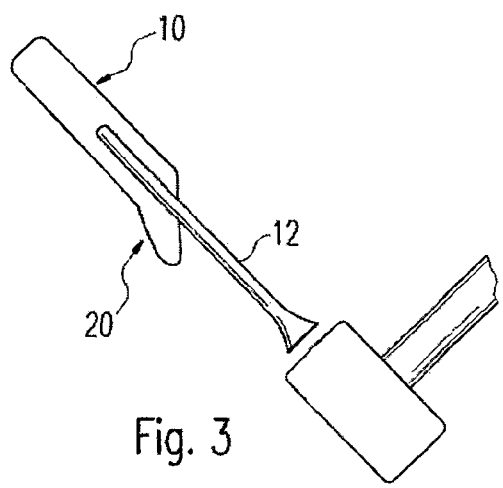

FIG. 2 shows how such a dental implant is inserted into a bone 1. For this purpose a cylindrical or (in the case of another appropriate configuration) slightly conical hole is bored into the bone and the dental implant is inserted. For this purpose a channel 11, in particular a cylindrical bore, has been formed within the dental implant so that a driving-in pin 12 can be inserted therein. This driving-in pin 12 is used to hold the dental implant and assist its fixation when beaten by a small hammer (see FIG. 3).

The final step is to put the supraconstruction into place.

This embodiment of the invention, in which the channel 11 to receive the driving-in pin 12 also passes through the abutment 20, is especially advantageous when (as shown in FIG. 2) an implant is to be inserted into the front part of the upper jaw, because there it is usually necessary for the abutment to be set at an angle. In this case the shaping is done by means of DVT/CT and computer in such a way that the patient is "measured" and an optimally fitting dental implant is designed by an appropriate computer simulation. In accordance with the virtual implant, the real implant is then produced from zirconium oxide in the dental laboratory.

Figure 4:
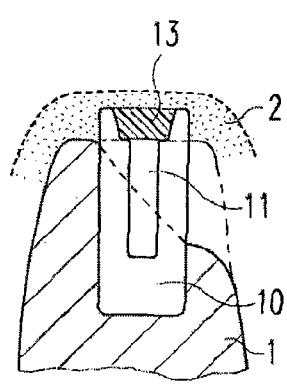
FIG. 4 is a schematic representation of an inserted anchoring part with bone and gum tissue.

The alternative form of the invention shown in FIG. 4 is intended to counteract a defect in the bone 1, so as to produce a bone structure corresponding to the dashed line in FIG. 4. For this purpose, an anchoring part 10 corresponding to the data obtained from the digital images is provided with special surfaces 4 such that osteogenesis occurs or is facilitated in the previously calculated regions. The anchoring part 10 thus constructed is then inserted into the bone, whereupon the channel 11 is closed by a silicone stopper 13. After insertion the gum tissue is closed over the implant. This closure results in an improved bone structure when the implant projects into the oral cavity during the healing phase. The silicone stopper 13 prevents the gum tissue from growing into the channel 11.

Figure 5:
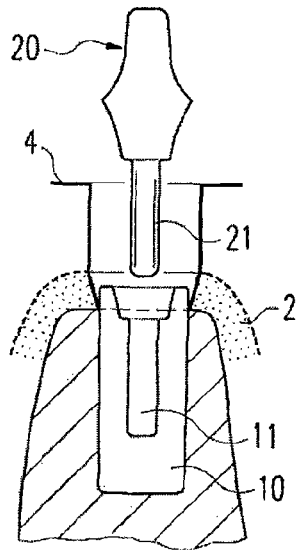
FIG. 5 is a sketch to assist with an explanation of how an abutment is inserted into the anchoring part.

After the phase during which the implant heals into the bone, the implant must again be exposed by means of a longitudinal section or punched hole (depending on the situation), as shown in FIG. 5. Now the abutment 20, which is made of zirconium oxide and is integral with a retaining piece 21, is cemented into the anchoring part 10, i.e. into the channel 11 provided therein, with the assistance of an adjustment tubule made of plastic; in this process, the plastic adjustment tubule in particular guarantees a blood-free working surface. After the remnants of cement have been removed, a provisional element can be cemented directly to the abutment 20. A particular advantage in this case is that a transmission impression of the implant is not needed, because all the parts can be put into final form in advance, in the dental laboratory, on the basis of the data obtained, which include models with measurement of the mucosa thickness or DVT/CT data.

Figure 6:
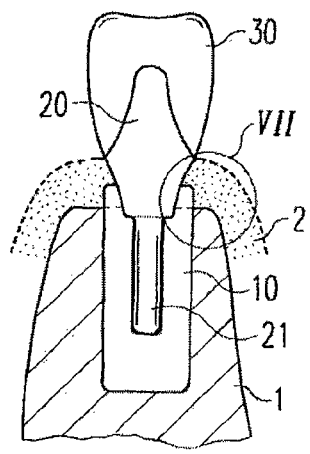
FIG. 6 is a schematic representation of the dental implant in a completely inserted state.
Figure 7:
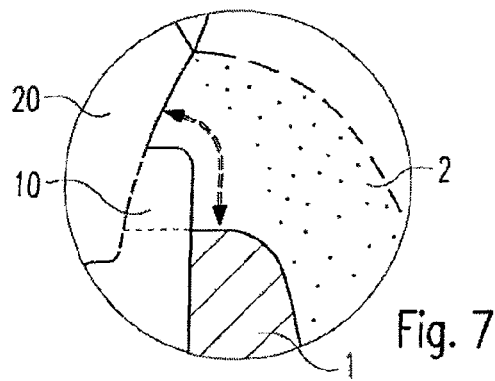
FIG. 7 is a view to an enlarged scale of the circled section labelled VII in FIG. 6.

The connection between anchoring part 10 and abutment 20 has a so-called "platform switch" such as is indicated in FIGS. 6 and 7, because now an adhesive connection has been produced between abutment 20 and anchoring part 10 that can cause irritation of the tissues. This is known in implantology, where studies have shown that the bone can become removed by ca. 1.6 to 2 mm from such a source of disturbance. Therefore the distance from the adhesion fissure to the bone should be set at ca. 1.5 to 2 mm (see double arrow in FIG. 7), to prevent the bone from decomposing in the region around the implant.

In the embodiment of the invention shown here another advantage that should be mentioned is that because of the rotationally symmetrical configuration of the anchoring part 10 (without screw thread) small changes of angle of rotation can be performed by the dentist during insertion, so that the driving-in process employing the arrangement shown here, with a concentric channel 11, is an especially simple method of treatment, usable even with an abutment that is set at a pronounced angle.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. Method of manufacturing a dental implant, comprising the steps preparation of a digital representation of the dental implant, milling of a zirconium-oxide green compact corresponding to said digital representation but overdimensioned to compensate for shrinkage, roughening by sandblasting of at least one section of said zirconium-oxide green compact to promote at least one of bone fusion and ingrowth of the gum tissue into the implant, and burning/sintering of said roughened zirconium-oxide green compact after said roughening step.

2. The method according to claim 1, further comprising the step of constructing at least one bore in said zirconium-oxide green compact for receiving a pin to assist retention, guidance and driving-in of an anchoring part of the dental implant.

3. The method according to claim 1, further comprising production of a 3-dimensional, digital image of a region of bone and gum tissue of a patient, in which the dental implant is to be inserted.

* * * * *